United States Patent [19]

Konz et al.

[11] 4,204,076
[45] May 20, 1980

[54] HYDROQUINONE DIMETHYL ETHER

[75] Inventors: Elmar Konz, Bad Soden am Taunus; Rudolf Pistorius, Ober-Mörlen, both of Fed. Rep. of Germany

[73] Assignee: Hoechst Aktiengesellschaft, Frankfurt am Main, Fed. Rep. of Germany

[21] Appl. No.: 960,857

[22] Filed: Nov. 15, 1978

Related U.S. Application Data

[62] Division of Ser. No. 871,921, Jan. 24, 1978, Pat. No. 4,161,614.

[30] Foreign Application Priority Data

Jan. 26, 1977 [DE] Fed. Rep. of Germany ....... 2703077

[51] Int. Cl.$^2$ .............................................. C07C 41/00
[52] U.S. Cl. .................................................... 568/648
[58] Field of Search ................................. 568/651, 648

[56] References Cited

U.S. PATENT DOCUMENTS 4,057,586 11/1977 Pistorius .................. 568/648

OTHER PUBLICATIONS

Krekeler et al., Chemical Abstracts, vol. 84, (1976), 150343n.

Kirschke et al., Chemical Abstracts, vol. 84, (1976), 58270p.

Johannissian et al., Chemical Abstracts, vol. 25, (1931), 921–922.

*Primary Examiner*—Bernard Helfin
*Attorney, Agent, or Firm*—Curtis, Morris & Safford

[57] ABSTRACT

Cyclohexanedione-(1,4)-tetramethyl diketal of the formula

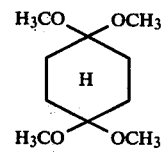

is obtained by catalytic hydrogenation of p-benzoquinone tetramethyl diketal in a basic medium, at a temperature of from about −10° to +150° C. The product gives cyclohexanedione-(1,4), on acid hydrolysis, which is a valuable starting product for various syntheses, for example for tetracyanoquinodimethane, a desired compound in the field of semiconductors.

Hydroquinone dimethyl ether, which is a valuable intermediate for the dyestuff preparation, is obtained from cyclohexanedione-(1,4)-tetramethyl diketal by catalytic dehydrogenation.

3 Claims, No Drawings

HYDROQUINONE DIMETHYL ETHER

This is a division, of application Ser. No. 871,921, filed Jan. 24, 1978 and now U.S. Pat. No. 4,161,614.

p- Benzoquinone tetramethyl diketal of the formula

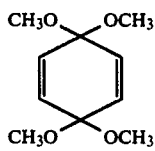

may be prepared, for example by anodic oxidation of anisol or of hydroquinone dimethyl ether in methanol/KOH according to N. L. Weinberg and B. Belleau, Tetrahedron 29 (1973), pages 279 to 285. The compound (I) may be prepared especially suitably by anodic oxidation of benzene, likewise in methanolic solution, this process, however requiring special conductive salts (cf. British Pat. No. 836,949).

The catalytic reduction of (I) with hydrogen in a neutral to slightly acidic medium with stoichiometric consumption of hydrogen give hydroquinone dimethyl ether in good yield (cf. German Offenlegungsschrift No. 25 47 464), which is a desired intermediate for the preparation of dyestuffs. It is quite natural that the catalytic reduction of (I) to hydroquinone dimethyl ether in a neutral to slightly acidic medium is advisable only when anisol or, in particular, benzene is used as the starting compound. Said catalytic reduction, however, involves some difficulties, since frequently an undesired decomposition of (I) occurs. When further investigating the reaction possibilities of (I), in particular during the catalytic hydrogenation, it has been found surprisingly that the catalytic hydrogenation in a basic medium results in a product which is completely different from that obtained in hydrogenation in a neutral to slightly acidic medium, namely cyclohexane-(1,4)-dione tetramethyl diketal of the formula

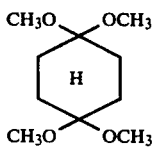

The present invention, consequently, provides a process for the preparation of cyclohexanedione-(1,4)-tetramethyl diketal of the formula (II) which comprises reducing p-benzoquinone tetramethyl diketal of the formula (I) with hydrogen in the presence of a hydrogenation catalyst, in a basic medium, at a temperature of from about −10° to +150° C., preferably of from about +10° to 50° C., in particular of from about +15° to +40° C.

The reduction may suitably be carried out in solvents of usual purity which are conventional for use for catalytic hydrogenation such as, for example, acetic acid methyl and ethyl esters, dioxane, tetrahydrofuran, etc. Preferred solvents are methanol and the reaction product (II) itself. Generally the solutions used for the reaction contain of from about 10 to 80% by weight, preferably of from about 20 to 50% by weight, of the compound (I).

Preferred catalysts are the noble metal catalysts belonging to group VIII of the periodic table which are conventional for use for catalytic hydrogenations, as well as their oxides, with or without a carrier material, for example active carbon. Preferred catalysts are palladium and platinum. A suitable catalyst which does not belong to said group is in particular Raney-nickel. The catalysts are used in usual amounts, preferably in an amount of from about 0.005 to about 0.2% by weight (metal), calculated on the starting compound (I).

The pH of the hydrogenation solution is adjusted at a value greater than 7 by the addition of a base. A pH in the range of from about 8 to 10, measured with humid pH paper, is preferred. Suitable bases are the conventional inorganic or organic bases, for example alkali metal hydroxides or alcoholates such as NaOH, KOH, NaOCH$_3$, KOCH$_3$, NaOC$_2$H$_5$ and others or nitrogen bases, for example triethylamine, cyclohexylamine, pyridine and others. They are generally used in an amount of from about 0.0001 to 5% by weight, preferably of from about 0.01 to 2% by weight, in particular of from about 0.1 to 1% by weight, calculated on the substance (I).

The hydrogenation takes place already under a hydrogen pressure of from about 0.2 to about 200 bars and more. A pressure of from about 1 to 100 bars, in particular of from about 10 to 50 bars, is preferred.

The hydrogenation proceeds according to the gross equation

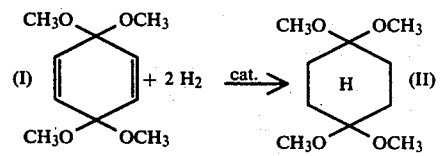

and is performed under said conditions until about 1.9 to 2.0 mols of hydrogen per mol of compound (I) are consumed or until no more hydrogen is consumed. As hydrogenation devices there may be used apparatuses which are conventional for reactions of this type, for example agitator or shaking autoclaves or adequate glass or enamel vessels provided with a stirrer. Upon completion of the hydrogen absorption, the reaction product is treated in known manner, for example by cooling and expanding the reaction vessel, filtering off the catalyst, distilling off the solvent and by subsequently distilling or crystallizing the compound obtained of the formula (II).

The cyclohexanedione tetramethyl diketal is an interesting intermediate which is variable in use. Cyclohexanedione-(1,4), in particular, which is generally difficulty obtainable, can be prepared from said diketal in good yield by acid hydrolysis, for example in aqueous methanol, in the presence of a trace of a mineral acid, for example H$_2$SO$_4$ or HCl at a pH lower than 7 and at a temperature of from 30° to 40° C., for example. This diketal is a desired starting product for syntheses in the field of semiconductors (for example tetracyanoquinodimethane, cf. J. Am. Chem. Soc. 84 (1962), 3372). On the other hand, hydroquinone dimethyl ether, which is a valuable intermediate for dyestuff preparation, in particular for the preparation of yellow pigment dyestuffs, may be obtained likewise in good yield, from the compound II by catalytic dehydrogenation and splitting off of methanol. These processes, which proceed according to the gross equation

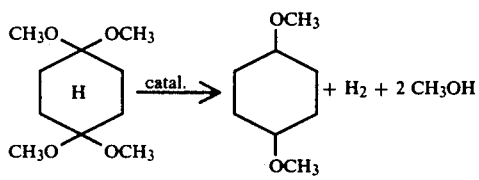

succeed in the presence of known (hydrogenation) and dehydrogenation catalysts, especially Pd catalysts, for example supported by active carbon, at a reaction temperature of from about 200° to 300° C., especially of from about 230° to 260° C., by simply refluxing (II) in a slight inert gas atmosphere, for example nitrogen. The reaction time essentially depends on the catalyst quantity employed and is generally in the range of from about 0.001 to 1% by weight, preferably of from about 0.01 to 0.1% by weight, calculated on the compound (II). Upon completion of the dehydrogenation and splitting off of methanol, the catalyst is filtered off and the reaction product is purified, for example by distillation. The latter method comprises two reaction steps: a catalytic hydrogenation of (I) in a basic medium to yield the compound (II) and a subsequent catalytic dehydrogenation and splitting off of methanol to yield hydroquinone dimethyl ether whereas the initially described catalytic hydrogenation of (I) in a neutral to slightly acidic medium yields directly hydroquinone dimethyl ether in one step. The preparation of hydroquinone dimethyl ether via the intermediate cyclohexane-(1,4)-dione-tetramethyl diketal, however, proceeds more uniformly and can be more readily repeated.

The following examples illustrate the invention:

EXAMPLE 1

398 (1.99 mols) of p-benzoquinone tetramethyl diketal are dissolved in 1000 g of methanol and, after addition of 1 ml of triethylamine and 1 g of Pd supported by active carbon (in 5% concentration), hydrogen is introduced under pressure while stirring, until a pressure of 50 atmospheres is set up. After absorption of 46.8 liters of hydrogen (liters measured under normal conditions of temperature and pressure), within a period of 30 minutes, at a temperature of from 20° to 40° C., the reactor is expanded, the catalyst is filtered off and the solvent (methanol) is distilled off under atmospheric pressure. When cooling the residue, cyclohexanedione-(1,4)-tetramethyl-diketal (345 g), which has a melting point of 75° C. is obtained in a crystalline form. The mother liquor comprises 30% by weight of hydroquinone dimethyl ether and 65% by weight of cyclohexanedione-(1,4)-tetramethyldiketal. The total yield, consequently, is 92.5% of the theory.

EXAMPLE 2

To 412 g of p-benzoquinone tetramethyl diketal, dissolved in 630 g of methanol, are added 1.5 g of freshly prepared Raney-nickel and 5 g of sodium methylate and hydrogen is introduced under pressure, at room temperature, while stirring, until a pressure of 70 atmospheres is attained. Within half an hour 40.5 liters of hydrogen have been absorbed while the temperature has increased to 38° C. Thereafter the pressure in the reactor is released, the catalyst is filtered off and the solvent is evaporated. Cyclohexanedione-(1,4)-tetramethyl diketal is obtained in a pure crystalline form in a yield of 79% of the theory (332 g). The mother liquor contains among others some hydroquinone dimethyl ether and a further 29 g of cyclohexanedione-(1,4)-tetramethyl diketal. The total yield of the reaction product, consequently, is 86% of the theory.

EXAMPLE 3

50 g of p-benzoquinone tetramethyl diketal are dissolved in 150 ml of methanol, 1 g of NaOCH$_3$ and 1 g of Pd/C (in a concentration of 5%) are added and hydrogenation is carried out while shaking under a hydrogen pressure of 15 atmospheres until hydrogen is absorbed no longer. The reactor is expanded, the catalyst is filtered off, the solvent is evaporated and the crystalline mass is recrystallized from a little methanol. The total yield of cyclohexanedione-(1,4)-tetramethyl diketal is 45.9 g which corresponds to a yield of 90% of the theory.

EXAMPLE 4

Cyclohexanedione-(1,4) from cyclohexanedione-(1,4)-tetramethyl diketal 50 g of cyclohexanedione-(1,4)-tetramethyl diketal are suspended in 150 ml of methanol, 20 ml of 1 N H$_2$SO$_4$ are added and the batch is stirred for 3 hours at 40° C. By recrystallization from ethanol are obtained 20 g of cyclohexanedione-(1,4) which corresponds to a yield of 74% of theory. The melting point is 78° C.

EXAMPLE 5

Hydroquinone dimethyl ether from cyclohexanedione-(1,4)-tetramethyl diketal 40 g of cyclohexanedione-(1,4)-tetramethyl diketal are refluxed with 1 g of Pd/C (of 5% concentration) at 230° C. At the same time a slight nitrogen current is passed through the reaction bath. Subsequently the mixture is distilled in vacuo (60 torrs, 131° C.). There is obtained 21 g of hydroquinone dimethyl ether (86% of the theory) in addition to 4 g of unmodified starting product.

What is claimed is:

1. A method of preparing hydroquinone dimethyl ether, which comprises catalytically dehydrogenating cyclohexanedione-(1,4)-tetramethyl diketal and splitting off methanol.

2. The method as defined in claim 1 in which the catalyst is palladium.

3. The method as defined in claim 1 in which the dehydrogenation is carried out with a palladium catalyst supported on active carbon at a reaction temperature of about 200° to 300° C.

* * * * *